United States Patent [19]

Puritch et al.

[11] Patent Number: 4,861,762
[45] Date of Patent: Aug. 29, 1989

[54] INSECTICIDE MIXTURES CONTAINING FATTY ACIDS

[75] Inventors: George S. Puritch, Brentwood Bay; Sergi F. Condrashoff, Victoria, both of Canada

[73] Assignee: Safer, Inc., Wellesley, Mass.

[21] Appl. No.: 218,093

[22] Filed: Jul. 12, 1988

Related U.S. Application Data

[63] Continuation of Ser. No. 118,305, Nov. 6, 1987, Pat. No. 4,774,234, which is a continuation of Ser. No. 722,460, Apr. 12, 1985, abandoned.

[51] Int. Cl.$^4$ ............................................. A01N 57/00
[52] U.S. Cl. .................................................... 514/122
[58] Field of Search ........................................ 514/122

[56] References Cited

U.S. PATENT DOCUMENTS

| | | | |
|---|---|---|---|
| 1,589,866 | 6/1926 | Siegler et al. | 514/558 |
| 2,345,891 | 4/1944 | Sullivan et al. | 514/558 |
| 2,345,892 | 9/1902 | Sullivan et al. | 424/45 |
| 2,345,894 | 4/1944 | Sullivan et al. | 424/45 |
| 2,345,902 | 4/1944 | Sullivan et al. | 424/45 |
| 2,345,905 | 4/1944 | Sullivan et al. | 424/45 |
| 2,345,907 | 4/1944 | Sullivan et al. | 424/45 |
| 2,345,908 | 4/1944 | Sullivan et al. | 424/45 |
| 2,345,909 | 4/1944 | Sullivan et al. | 424/45 |
| 3,429,970 | 2/1969 | Ruegg et al. | 514/703 |
| 3,541,154 | 11/1970 | Ruegg et al. | 260/583 |
| 3,801,652 | 4/1974 | Ruegg | 260/514 R |
| 3,887,710 | 6/1975 | Shaver | 514/481 |

FOREIGN PATENT DOCUMENTS 950357  7/1974  Canada .

OTHER PUBLICATIONS

Windholz, The Merck Index, An Encyclopedia of Chemicals, Drugs, and Biologicals; 10th Edition, p. 813 (1983).

Puritch, Pesticidal Soaps and Adjuvants—What are They and How Do They Work?; Proceedings of the 23rd Annual Lower Mainland Horticulture Improvement Association Growers' Short Course—Feb. 11, 12, 13, 1981, pp. 53–67.

Puritch, Biocidal Effects of Fatty Acid Salts on Various Forest Insect Pests; Chapter 10, reprinted from Symposium on the Pharmacological Effects of Lipids, AOCS Monograph No. 5, pp. 105–112 (1978).

*Primary Examiner*—Allen J. Robinson
*Attorney, Agent, or Firm*—Lahive & Cockfield

[57] ABSTRACT

Mixtures of organic insecticides of the organophosphate types or of the carbamate type, with certain fatty acids or their salts, have been found to have enhanced insecticidal activity. The fatty acids found operative are the unsaturated 18-carbon atom ones. The mixtures are toxic to both sucking insects and defoliators. The weight ratio of organophosphate or carbamate to fatty acid can range from about 1:1 to about 1:200 respectively. The amounts of the organophosphate or carbamate required for substantial effectiveness can be reduced significantly by concurrent use of the fatty acid. The fatty acid is more environmentally acceptable than the other types of insecticides mentioned. This unique composition can be used to protect against a broader range of insects.

13 Claims, No Drawings

INSECTICIDE MIXTURES CONTAINING FATTY ACIDS

This application is a continuation of copending application Ser. No. 118,305, filed Nov. 6, 1987, now U.S. Pat. No. 4,774,234 issued Sept. 27, 1988, which in turn is a continuation of Ser. No. 722,460, filed Apr. 12, 1985, now abandoned.

FIELD OF THE INVENTION

This invention is concerned with insecticides and enhancing their insecticidal effect using partial replacement compounds which are more environmentally acceptable.

INFORMATION DISCLOSURE STATEMENT

One of the main means of controlling insect infestation has been through the use of chemical insecticides. At the present time there are 15,000 registered pesticides within North America of which about 6,000 are sold in Canada. The pesticides generally fall into five major categories viz: chlorinated hydrocarbons e.g. DDT, lindane, methoxychlor, etc.; organophosphates e.g. malathion, dibrom, diazinon (trademark), phosphamidon, etc.; carbamate compounds e.g. baygon (trademark), sevin (trademark), zectran (trademark), etc.; inorganic compounds e.g. arsenic, sulphur, borax, etc.; and botanical compounds e.g. pyrethrum, strychnine, nicotine, etc. The chemical insecticides have been frequently used against major forest pests, e.g. DDT against spruce budworm, and have in many cases, been quite successful.

The chemical insecticides, with the exception of the botanical ones, have several disadvantages. Most of them are highly toxic to fish, wildlife, and humans and must be used with caution. They are usually not natural biological constituents and tend to persist for long lengths of time after their initial application. This is best exemplified by the chlorinated hydrocarbons which because of their persistence have passed through the animal food chain and caused egg shell thinning and egg breakage in many species of birds.

Besides their initial toxic effect, these compounds can have sub-acute effects on non-target fauna and flora thereby causing biochemical, behavioural and physiological changes as well as reproductive failure. Most of the chemical insecticides are quite expensive and with the current petroleum shortage, difficult to obtain. The breakdown products and secondary metabolites of most petrochemical pesticides and their impact on humans and other living organisms are poorly understood.

Recent research has shown that the unsaturated C18 fatty acids or their salts (C18:X) are highly toxic to soft bodied insects including aphids, mealybugs, whitefly, pear psylla, rose slugs, etc. (G. Puritch, 1978 Symposium on the Pharmacological Effects of Lipids AOCS monograph No. 5, 105-112). During investigations, it was further discovered that combination of the unsaturated 18 carbon fatty acids and/or salts with either organophosphates or carbamate insecticides have an unexpectedly high degree of insecticidal activity when topically applied. This unique finding has permitted a reduction of the petrochemical pesticide required for suitable pest control and has provided an increase in the spectrum of insect pests controlled. For example, we found the C18:X acids, especially oleic and linoleic and their salts in solution in concentrations from 0.25 to 5.0% in combination with the organophosphates, especially diazinon in a concentration range of 50 ppm to 50,000 ppm, were effective for the control of insect pests.

SUMMARY OF THE INVENTION

The invention thus provides an insecticidal composition having enhanced insecticidal activity comprising:

(a) an insecticide active against defoliating insects selected from the group consisting of organic esters of phosphoric or thiophosphoric acid and carbamates, and mixtures thereof, and (b) an unsaturated fatty acid having 18 carbon atoms or its salt; the fatty acid being at least about 50% by weight of (a)+(b).

The invention includes a method of protecting susceptible plants against sucking insects or defoliating insects applying concurrently to the plant surfaces or directly to the insects, both (a) an insecticide active against defoliating insects selected from organic esters of phosphoric or thiophosphoric acids and carbamates, and mixtures thereof, and (b) an unsaturated fatty acid having 18 carbon atoms or its salt; the fatty acid compound being at least about 50% by wt. of (a)+(b). Preferably (a) and (b) are applied together as a mixture.

The invention also includes a method of synergistically enhancing the insecticidal activity of an insecticide selected from the group consisting of organic esters of phosphoric or thiophosphoric acid and carbamates and carbamates and mixtures thereof, the method comprises adding to the insecticide an effective amount of a unsaturated fatty acid having 18 carbon atoms. In any case, the amount of the unsaturated fatty acid is at least the same amount as the insecticide.

The fatty acid (b) is preferably selected from oleic acid, linoleic acid, their soaps (salts) and mixtures thereof. Linolenic acid or ricinoleic acid may be present. The cation forming the salt or soap with the fatty acid usually is sodium, potassium or ammonium. Practically, it is possible to use an unsaturated fatty acid having 18 carbon atoms in admixture with a small amount of a saturated fatty acid having about 18 carbon atoms.

Particularly preferred is a mixture of the salts of oleic acid and linoleic acid. One of the most convenient mixture of the salt contains from about 50 to about 80% by weight of oleic acid and 40 to 5% by weight of linoleic acid, the balance being a small amount, say, at most 20% by weight of, a saturated fatty acid, for example, palmitic acid and stearic acid.

In the composition, or in use, the proportions of insecticide (a) to fatty acid (b) may range from about 1:200 to about 1:1 by wt., preferably about 1:20 to about 1:2.

The mixture may be used in the form of a solution in any suitable solvent. In one preferred embodiment an aqueous solution is used in which the concentration of insecticide (a) ranges from about 0.0005 to about 5% preferably from about 0.005 to about 0.1% by wt., and the concentration of fatty acid or its salt (b) ranges from about 0.05 to about 5, preferably from about 0.1 to about 1% by wt. Preferably the soap of the fatty acid is used in aqueous solution.

Other detergents, wetting agents, carriers, adjuvants, etc., may be used as known in the art.

Suitable insecticidal esters of phosphoric and thiophosphoric acids include diazinon ® [phosphorothioic acid O,O-diethyl-O-(2-isopropyl-6-methyl-4-pyrimidinyl) ester], malathion [S-(1,2-dicarbethoxyethyl)-O,O-dimethyldithiophosphate], phosphamedon.

Suitable carbamate insecticides include carbaryl(-sevin ®) [1-naphthyl-N-methylcarbamate)], pirimicarb 2(dimethylamino)-5, 6-dimethyl-4-pyrimidyl dimethyl-carbamate.

Because the unsaturated fatty acid (b) used according to the present invention is biodegradable and the amount of the synthetic insecticide (a) may be substantially reduced in order to obtain satisfactory insecticidal results, it is expected that the present invention will, at least partly, the environmental problem which has arisen as a result of the massive use of the synthetic insecticide (a) which is hardly biodegradable.

EXAMPLE 1

Test of unsaturated C18 salts (SIS=oleate/linoleate, 77%:7%) in combination with the organophosphate insecticide, diazinon ® [phosphorothioic acid O,O-diethyl-O-(2-isopropyl-6-methyl-4-pyrimidinyl) ester]

| (1) Tap water control (=diluent) | (11) 0.1% SIS + 0.0025 |
|---|---|
| (2) 0.1. SIS | (12) 0.1 SIS + 0.005 DZ |
| (3) 0.25 SIS | (13) 0.25 SIS + 0.0005 DZ |
| (4) 0.5 SIS | (14) 0.25 SIS + 0.001 DZ |
| (5) 0.0005 DZ | (15) 0.25 SIS + 0.0025 DZ |
| (6) 0.001 DZ | (16) 0.25 SIS + 0.005 DZ |
| (7) 0.0025 DZ | (17) 0.50 SIS + 0.0005 DZ |
| (8) 0.005 DZ | (18) 0.50 SIS + 0.001 DZ |
| (9) 0.1 SIS + 0.0005 DZ | (19) 0.50 SIS + 0.0025 DZ |
| (10) 0.1 SIS + 0.001 DZ | (20) 0.50 SIS + 0.005 DZ |

*: a.i.=active ingredient.

RESULTS

The results are listed in Table 1. All of the unsaturated C18 salts (SIS)-diazinon combinations gave higher mortality than the sum of the mortalities obtained for SIS or diazinon alone, thus they acted synergistically (Table 1).

TABLE 1

Observed and corrected mortality of the cabbage aphid, *Brevicoryne brassicae* (L.) to treatment solutions of SIS and Diazinon at various concentrations of active ingredient. Assessments made 24 hours post-treatment.

| Treatment | Mortality Per Replicate | | | | | Percent Mortality | Abbott's Corrected Mortality | Expected Additive Mortality |
|---|---|---|---|---|---|---|---|---|
| | 1 | 2 | 3 | 4 | 5 | | | |
| 0.1 SIS + 0.005 DZ | 20/20 | 20/20 | 20/20 | 20/20 | 20/20 | 100 a 1/ | 100 2/ | 52.3 |
| 0.5 SIS + 0.005 DZ | 20/20 | 20/20 | 20/20 | 20/20 | 20/20 | 100 a | 100 2/ | 84.8 |
| 0.5 SIS + 0.0005 DZ | 19/20 | 20/20 | 18/18 | 19/19 | 20/20 | 99.0 a | 98.8 2/ | 70.7 |
| 0.25 SIS + 0.0025 DZ | 20/20 | 19/19* | 19/19* | 18/19* | 20/20 | 99.0 a | 98.8 2/ | 56.9 |
| 0.5 SIS + 0.001 DZ | 20/20 | 20/20 | 18/20 | 20/20 | 20/20 | 98.0 a | 97.7 2/ | 68.2 |
| 0.25 SIS + 0.001 DZ | 20/20 | 20/20 | 18/20 | 18/18* | 19/19* | 97.9 a | 97.5 2/ | 33.5 |
| 0.1 SIS + 0.0025 DZ | 18/18* | 18/18* | 18/19* | 20/20 | 19/20* | 97.9 a | 97.5 2/ | 59.1 |
| 0.5 SIS + 0.0025 DZ | 17/20 | 20/20 | 20/20 | 20/20 | 19/19* | 97.0 a | 96.5 2/ | 91.6 |
| 0.25 SIS + 0.005 DZ | 17/20 | 19/20 | 20/20 | 20/20 | 20/20 | 96.0 a | 95.3 2/ | 50.1 |
| 0.1 SIS + 0.0005 DZ | 12/19 | 19/20 | 18/20 | 17/17* | 18/19 | 88.4 ab | 86.5 2/ | 38.2 |
| 0.25 SIS + 0.0005 DZ | 13/19* | 14/20 | 17/20 | 16/20 | 19/19* | 80.6 b | 77.4 2/ | 36.0 |
| 0.1 SIS + 0.001 DZ | 19/19* | 19/20 | 13/19* | 10/19* | 13/17* | 78.7 b | 75.1 2/ | 35.7 |
| 0.5 SIS | 10/22 | 9/15* | 9/20* | 8/19* | 14/20 | 58.1 c | 43.8 | |
| 0.0025 DZ | 11/20 | 10/20 | 10/20 | 12/18* | 9/16* | 55.3 c | 47.8 | |
| 0.005 DZ | 5/15* | 8/19* | 7/15* | 7/16* | 14/18* | 49.4 cd | 41.0 | |
| 0.0005 DZ | 5/20 | 8/19 | 6/20 | 9/20 | 9/20 | 37.4 de | 26.9 | |
| 0.001 DZ | 8/16 | 6/15* | 6/19* | 4/20 | 7/18* | 35.2 e | 24.4 | |
| 0.1 SIS | 1/19* | 3/19* | 5/19 | 2/20 | 5/19* | 24.0 f | 11.3 | |
| 0.25 SIS | 6/20 | 3/15 | 4/18* | 1/4* | 3/20 | 22.1 f | 9.1 | |
| Control-tap water (=diluent) | 1/17 | 4/18* | 1/20 | 2/18 | 4/11* | 14.3 f | 0 | |

*Total # (20) of aphids altered due to discounting aphid parasitism and presence of the potato aphid.
1/ Means followed by the same letter are not significantly different at the 5% alpha level as determined by Duncan's multiple range test.
2/ Mortality values (corrected) followed by the superscript 2 are greater than additive i.e. synergistic for the control of the cabbage aphid, *Brevicoryne brassicae* (L.).

SAMPLE UNIT AND PROCEDURE

Twenty treatments, five replicates per treatment were applied to cabbage aphids, *B. brassicae* (L.) using the standardized plate method. This method entailed placing greater than twenty insects per replicate onto a glass plate (40×40 cm) and applying approximately 1 ml of treatment solution per replicate using a 10 cc plastic syringe equipped with a furnace-burner-tip nozzle (Monarch 0.75 GPH, 45° A.R.). One minute after the spray was applied, twenty insects were transferred to filter paper-lined petri plates. Petri plates were left covered with mortality assessments made 24 hours post-treatment discounting parasitized aphids and potato aphids, *Macrosiphum euphorbiae* (Thomas). Treatments applied were (% a.i.*):

EXAMPLE 2

Test of unsaturated C18 salts (SIS=oleate/linoleate, 77%:7%) in combination with the organophosphate insecticide, diazinon ® [Phosphorothioic acid O,O-diethyl-O-(2-isopropyl-6-methyl-4-pyrimidinyl) ester] for the control of the larval form of the tent caterpillar, *Malacosoma californicum pluviale* (Dyar) tested in vitro.

SAMPLE UNIT AND PROCEDURE

Tent caterpillars, *Malacosoma californicum pluviale* (Dyar) were field collected from their hawthorn host, *Crataegus douglasii* L. and brought to an entomology laboratory where they were caged and fed prior to testing. Five replicates per treatment with each replicate containing five caterpillars were randomly assigned to the following treatments (% a.i.):

| | |
|---|---|
| 1. water control (diluent) | 11. 0.1 SIS + 0.001 DZ |
| 2. control (untreated) | 12. 0.1 SIS + 0.0025 DZ |
| 3. 0.1 SIS | 13. 0.1 SIS + 0.005 DZ |
| 4. 0.25 SIS | 14. 0.25 SIS + 0.0005 DZ |
| 5. 0.5 SIS | 15. 0.25 SIS + 0.001 DZ |
| 6. 0.0005 DZ | 16. 0.25 SIS + 0.0025 DZ |
| 7. 0.001 DZ | 17. 0.25 SIS + .005 DZ |
| 8. 0.0025 DZ | 18. 0.5 SIS + 0.0005 DZ |
| 9. 0.005 DZ | 19. 0.5 SIS + 0.001 DZ |
| 10. 0.1 SIS + 0.0005 DZ | 20. 0.5 SIS + 0.0025 DZ |
| | 21. 0.5 SIS + 0.005 DZ |

The standardized plate method (see example 1) was used in testing the solutions with ca. 3 ml of solution being applied per replicate. Mortality assessments were made 24 and 48 hours after treatments.

TABLE 2

Mortality of tent caterpillar larvae, *Malacosoma californicum pluviale* (Dyar) to treatment solutions of SIS and Diazinon at various concentrations of active ingredient. Assessment made 48 hrs. post-treatment.

| Date of Trt. | Treatment | Mort. Per Rep. (X/5) | | | | | % Mort. |
|---|---|---|---|---|---|---|---|
| | | 1 | 2 | 3 | 4 | 5 | |
| June 5/84 | Control-tap water | 0 | 0 | 0 | 0 | 0 | 0.0 |
| | Control-untreated | 0 | 0 | 0 | 0 | 0 | 0.0 |
| | 0.1 SIS | 0 | 0 | 0 | 0 | 0 | 0.0 |
| | 0.25 SIS | 1 | 0 | 0 | 1 | 1 | 12.0 |
| | 0.50 SIS | 0 | 1 | 0 | 0 | 0 | 4.0 |
| | 0.0005 DZ | 0 | 0 | 0 | 0 | 0 | 0.0 |
| | 0.001 DZ | 0 | 0 | 0 | 0 | 0 | 0.0 |
| | 0.0025 DZ | 0 | 0 | 1 | 0 | 2 | 12.0 |
| | 0.005 DZ | 4 | 3 | 4 | 2 | 3 | 64.0 |
| | 0.1 SIS + 0.0005 DZ | 3 | 2 | 4 | 0 | 2 | 55.0 |
| | 0.1 SIS + 0.001 DZ | 2 | 2 | 2 | 1 | 3 | 40.0 |
| | 0.1 SIS + 0.0025 DZ | 5 | 4 | 5 | 5 | 5 | 96.0 |
| | 0.1 SIS + 0.005 DZ | 5 | 5 | 4 | 5 | 5 | 96.0 |
| | 0.25 SIS + 0.0005 DZ | 3 | 3 | 1 | 2 | 3 | 48.0 |
| | 0.25 SIS + 0.001 DZ | 3 | 3 | 2 | 3 | 5 | 64.0 |
| | 0.25 SIS + 0.0025 DZ | 4 | 3 | 1 | 4 | 4 | 64.0 |
| | 0.25 SIS + 0.005 DZ | 5 | 4 | 5 | 5 | 5 | 96.0 |
| | 0.50 SIS + 0.0005 DZ | 4 | 4 | 2 | 5 | 5 | 80.0 |
| | 0.50 SIS + 0.001 DZ | 3 | 4 | 5 | 5 | 2 | 76.0 |
| | 0.50 SIS + 0.0025 DZ | 5 | 5 | 4 | 4 | 5 | 92.0 |
| | 0.50 SIS + 0.005 DZ | 5 | 5 | 5 | 5 | 5 | 100.0 |

TABLE 3

Expected values (additive) versus observed values of percent mortalities obtained for tent caterpillar larvae, *Malacosoma californicum pluviale* (Dyar) when treated with different SIS/DZ combinations. Expected values were calculated from results of SIS and DZ alone.

| Treatment | Observed Mortality | Expected Additive Mortality |
|---|---|---|
| 0.1 SIS + 0.0005 DZ | 55* | 0 |
| 0.1 SIS + 0.001 DZ | 40* | 0 |
| 0.1 SIS + 0.0025 DZ | 96* | 12 |
| 0.1 SIS + 0.005 DZ | 96* | 64 |
| 0.25 SIS + 0.0005 DZ | 48* | 12 |
| 0.25 SIS + 0.001 DZ | 64* | 12 |
| 0.25 SIS + 0.0025 DZ | 64* | 24 |
| 0.25 SIS + 0.005 DZ | 96* | 76 |
| 0.50 SIS + 0.0005 DZ | 80* | 4 |
| 0.50 SIS + 0.001 DZ | 76* | 4 |
| 0.50 SIS + 0.0025 DZ | 92* | 16 |
| 0.50 SIS + 0.005 DZ | 100* | 68 |

*Numerical values followed by an asterisk are significantly greater than the expected additive values.

RESULTS

All of the unsaturated C18 salts (SIS)-diazinon combinations gave higher mortalities than the sum of the mortalities obtained for SIS or diazinon alone in the control of the larval form of the tent caterpillar, thus they acted synergistically (Table 3).

EXAMPLE 3

Test of unsaturated C18 salts (SIS=oleate/linoleate, 77%:7%) in combination with the organophosphate insecticide, diazinon® [phosphorothioic acid O,O-diethyl-O-(2-isopropyl-6-methyl-4-pyrimidinyl) ester) for the control of tent caterpillars, *Malacosoma californicum pluviale* (Dyar) tested in situ.

SAMPLE UNIT AND PROCEDURE

Tent caterpillars, *Malacosoma californicum pluviale* (Dyar) in various larval instars in their tents were tagged in the field on their host plant hawthorn, and randomly assigned to the following treatments (% a.i.):

| | |
|---|---|
| 1. Water control (=diluent) | 6. 0.1 DZ |
| 2. 1.0 SIS | 7. 1.0 SIS + 0.0025 DZ |
| 3. 0.0025 DZ | 8. 1.0 SIS + 0.005 DZ |
| 4. 0.005 DZ | 9. 1.0 SIS + 0.01 DZ |
| 5. 0.01 DZ | 10. 1.0 SIS + 0.1 DZ |

Each treatment consisted of three replicates, with the treatment solutions applied to the tent and caterpillars, using a 750 ml hand-held trigger spray pump and sprayed until the setae of the larvae were wet (ca. 50-60 ml of solution/tent). The weather was clear and sunny, 19°-20° C. with a 3-4 km hr. breeze and with no rain occurring during the experiment.

RESULTS

Synergistic effects of unsaturated C18 salts (SIS) and diazinon combinations were observed after treating tent caterpillars, *Malacosoma californicum pluviale* (Dyar) on trees in field conditions (Table 4). The combinations of 1.0% SIS with 1) 0.0025 DZ; 2) 0.005 DZ or 3) 0.01 DZ gave higher mortality than the sum of the mortalities of the components (i.e. SIS+diazinon) alone, thus they acted synergistically.

TABLE 4

Mortality of tent caterpillar larvae, *Malacosoma californicum pluviale* (Dyar) to treatment solutions of SIS and Diazinon at various concentrations of active ingredient tested in field conditions. Assessments made 24 hours post-treatment.

| Treatment | Replicates | | | % Mort. | Expected Additive Mortality |
|---|---|---|---|---|---|
| | 1 | 2 | 3 | | |
| water control (diluent) | 2/38 | 1/74 | 0/8 | 2.50 | |
| 1.0 SIS | 1/31 | 6/49 | 2/15 | 9.47 | |
| 0.0025 DZ | 1/78 | 1/4 | 1/11 | 3.22 | |
| 0.005 DZ | 0/2 | 1/ | 2/28 | 6.67 | |
| 0.01 DZ | 6/14 | 6/21 | 0/10 | 26.7 | |
| 0.1 DZ | 7/7 | 32/32 | 53/60 | 92.9 | |
| 1.0 SIS + 0.0025 DZ | 10/13 | 22/25 | 9/35 | 56.2* | 12.69 |
| 1.0 SIS + 0.005 DZ | 4/40 | 6/6 | 6/15 | 26.2* | 16.14 |
| 1.0 SIS + 0.01 DZ | 1/1 | 38/50 | 4/12 | 71.4* | 36.17 |
| 1.0 SIS + 0.1 DZ | 46/49 | 7/7 | 28/30 | 94.2 | >100 |

1/ Caterpillars had moved off leaving none in the tent so observation counted as missing.
*Values with an asterisk had mortalities greater than additive mortalitites, thus acted synergistically.

EXAMPLE 4

Test of unsaturated C18 salts (SIS=oleate/linoleate, 77%:7%) in combination with the organophosphate insecticide, diazinon for the control of the greenhouse whitefly, *Trialeurodes vaporariorum* Westwood.

SAMPLE UNIT AND PROCEDURE

Adult whitefly were vacuum aspirated into 30 dram vials, with 20-40 whitefly per vial. One vial of whitefly at a time was cooled at 0° c. in a freezer for 2-3 minutes, contents tapped into cooled filter-paper-lined petri plates, and sprayed with ca. 2 mls of one of the following treatment solutions, using a plastic disposable syringe sprayer adapted to a furnace-burner-tip-nozzle (Monarch 0.75 GPH, 45° AR) (a.i.):
1. Tap water control (=diluent)
2. 0.25% SIS
3. 0.0025% DZ
4. 0.25% SIS+0.0025% DZ After treatment, the exact whitefly number was recorded per petri plate, the cover placed on the dish and left 24 hours until assessment.

RESULTS

A higher mortality of whitefly adults (98.8%) was obtained in the combination of 0.25% SIS with 0.0025% DZ than the sum of the mortalities of the components alone (90.2%) indicating a synergistic interaction between the 0.25% SIS and 0.0025% DZ (Table 5).

TABLE 5

Mortality of the adult form of the greenhouse whitefly, *Trialeurodes vaporariorum* Westwood caused by treatments of unsaturated C18 salt (SIS) and the organophosphate, diazinon applied alone or in combination. Mortality was assessed 24 hours post treatment.

| Treatment | Replicate (% Mortality) | | | | | % Mort. ± S.E. | % Mort. Abbott's Correct. |
|---|---|---|---|---|---|---|---|
| | 1 | 2 | 3 | 4 | 5 | | |
| Tap water control (=diluent) | 64.7 | 22.2 | 41.5 | 18.4 | 36.1 | 36.6 ± 18.4 | 0 |
| 0.25% SIS | 89.3 | 82.8 | 97.4 | 84.0 | 84.4 | 87.6 ± 6.1 | 81.4 |
| 0.0025% DZ | 71.0 | 79.2 | 28.6 | 43.3 | 10.0 | 46.4 ± 28.9 | 8.8 |
| 0.25% SIS + 0.0025 DZ | 100 | 100 | 96.2 | 100 | 100 | 99.2 ± 1.7 | 98.8* |

*Mortality value followed by an asterisk is greater than the additive value of the two components alone, thus 0.25% SIS and 0.0025% DZ acted synergistically.

EXAMPLE 5

Test of unsaturated C18 fatty acid salts (soaps) in combination with diazinon ® for control of earwigs (*Forficula auricularia*).

MATERIALS AND METHODS

Adult *F. auricularia* were collected from the field and separated into groups of 25. Three replicates of each group were assigned to the following treatments (a.i.):
(a) water
(b) 0.8% C18:1+C18:2 (77.7%) salts (SIS)
(c) 0.01 Diazinon ® (DZ)
(d) 0.8% SIS+0.01% DZ Insects were treated topically to wetting with a hand pump sprayer and returned to rearing containers. Mortality was assessed after 24 hours at room temperature.

RESULTS

Results are given in Table 6.

TABLE 6

| | % Mortality | | | | | |
|---|---|---|---|---|---|---|
| Treatment | Rep 1 | Rep 2 | Rep 3 | Rep 4 | Rep 5 | Ave. |
| Control | 0* | 0 | 0 | 0 | 0 | 0 |
| 0.8% SIS | 20 | 40 | 20 | 40 | 0 | 24 |
| 0.01% DZ | 20 | 8 | 12 | 16 | 8 | 12.8 |
| 0.8% SIS + 0.01% DZ | 100 | 92 | 100 | 100 | 100 | 98.4 |

*% Mortality out of 25 insects.

These results clearly show the synergism between the fatty acid salts and diazinon ®.

EXAMPLE 6

Test of unsaturated C18 salts (BIS=oleate/linoleate, 54.0%:43.0%) in combination with the carbamate insecticide, pirimicarb for the control of the cabbage aphid, *Brevicoryne brassicae* (L.).

HOST PLANT

Cabbage, *Lactuca sativa* L.c.v. "Penn State Baldhead".

SAMPLE UNIT AND PROCEDURE

Twenty four cabbage plants, eight weeks in age, which were infested with the cabbage aphid, *B. brassicae* (L.) were selected from a commercial field (Mr. Ian Vantreight, 4423 Tyndall Road, Victoria, B.C.) and brought back to a greenhouse for testing. These plants were replanted and randomly assigned to the following treatments (% a.i.):
(a) Tap water control (=diluent for treatments)
(b) 0.06% BIS
(c) 0.13% BIS
(d) 0.006% pirimicarb (⅛ the label rate)
(e) 0.006% pirimicarb +0.06% BIS
(f) 0.006% pirimicarb +0.13% BIS These solutions were made up fresh before use. The unsaturated fatty acid salts were made by neutralizing oleic and linoleic (BIS=54.0%:43.0%) with potassium hydroxide. A standard retail grade of pirimicarb (Pirimor ®) formulated as a 50% WP was used in the tests. Treatments were applied with a hand-pump sprayer (Green Cross Super Spray 6X-60 ®) with each plant sprayed to wetting (ca. 10 mls treatment solution). Each treatment consisted of four replicates with one plant per replicate. Aphid mortality was assessed twenty-four hours after treatment with twenty-five aphids counted per replicate.

A significant treatment effect (P>0d.01%) was obtained from analysis of variance of the data, with the pirimicarb BIS combinations providing greater control of the cabbage aphid than each of the components (i.e. BIS and pirimicarb) alone (Table 7). By comparing the expected additive mortalities of the pirimicarb and BIS treatments (4% and 5%) with the observed mortalities (80% and 85) of the two pirimicarbs/BIS combinations, the synergistic interaction of the BIS with the pirimicarb is clearly evident. The pirimicarb/BIS combinations gave higher mortality than the sum of the mortalities obtained for pirimicarb and BIS alone, thus they act synergistically.

TABLE 7

Effect of the carbamate insecticide, pirimicarb and the C18 fatty acid salt (BIS) on cabbage aphid mortality.

| Treatment | Aphid Mortality (X/25) per replicate | | | | Mean # Dead (X/25) | Standard Error (±) | % Mortality Obtained | Expected Additive Mortality |
|---|---|---|---|---|---|---|---|---|
| | 1 | 2 | 3 | 4 | | | | |
| Tap water control (=diluent) | 0 | 0 | 2 | 0 | 0.5 | 1.0 | 2 a* | |
| 0.06% a.i. BIS | 0 | 2 | 1 | 0 | 0.75 | 0.96 | 3 a | |
| 0.13% a.i. BIS | 2 | 1 | 1 | 0 | 1.0 | 0.82 | 4 a | |
| 0.006% a.i. pirimicarb | 1 | 0 | 0 | 0 | 0.25 | 0.5 | 1 a | |
| 0.006% a.i. pirimicarb + 0.06% BIS | 19 | 20 | 21 | 20 | 20 | 0.82 | 80 b | 4 |
| 0.006% pirimicarb + 0.13% BIS | 21 | 20 | 21 | 23 | 21.25 | 1.26 | 85 b | 5 |

$F_S = 473.5**$; $F_c(5, 18)0.01 = 5.07$
*Means followed by the same letter are not significantly different at the 5% alpha level using Duncans Multiple Rang Test.
**Significant to the 0.01 alpha level

What I claim as my invention is:

1. An insecticidal composition having synergistic insecticidal activity, consisting essentially of:
   (a) an insecticide active against defoliating insects comprising, S-(1,2-dicarbethoxyethyl)-O,O-dimethyldithiophosphate; and
   (b) oleic acid, a salt thereof, or a mixture thereof
   wherein the weight proportion of said insecticide (a): said oleic acid or its salt (b) is from about 1:1,000 to about 1:1.

2. The composition of claim 1 further comprising a member selected from the group consisting of linoleic acid, linolenic acid, salts thereof, and mixtures thereof.

3. The composition of claim 1, wherein component (b) is a sodium, potassium or ammonium salt.

4. The composition of claim 3, wherein the weight proportion of said insecticide (a): said oleic acid or salt (b) is from about 1:1,000 to about 1:2.

5. The composition of claim 3, wherein the weight proportion of said insecticide (a): said oleic acid or salt (b) is from about 1:1,000 to about 1:20.

6. The composition of claim 3, wherein the weight proportion of said insecticide (a): said oleic acid or salt (b) is from about 1:200 to about 1:2.

7. The composition of claim 3 in the form of an aqueous solution in which the concentration of the insecticide (a) ranges from about 0.005 to about 5% by wt. and the concentration of the oleic acid or salt (b) ranges from about 0.05 to about 5;L % by wt.

8. A method of protecting susceptible plants against defoliating insects, which method comprises applying to the plant surfaces of directly to the insects, an insecticidally effective amount of a composition having synergistic insecticidal properties consisting essentially of both (a) an insecticide active against defoliating insects comprising S-(1,2-dicarbethoxyethyl)-O,O-dimethyldithiophosphate, and (b) oleic acid, its salts, or a mixture thereof,
   wherein the weight proportion of said insecticide (a): said oleic acid or its salt (b) is from about 1:1,000 to about 1:1, whereby said composition has an insecticidal effect greater than the additive effect of ingredients (a) and (b).

9. The method of claim 8, wherein component (b) is a sodium, potassium or ammonium salt.

10. The method of claim 9, wherein the weight proporton of said insecticide (a): said oleic acid or salt (b) is from about 1:1,000 to about 1:2.

11. The method of claim 9, wherein the mixture is in an aqueous solution containing from about 0.005 to about 5% by weight of the insecticide (a) and from about 0.05 to about 5% by weight of the oleic acid or salt and the proportion of (a):(b) by weight is within the range from 1:1,000 to 1:20.

12. The method of claim 11, wherein component (b) is a mixture consisting essentially of 50% to 80% by weight of oleic acid or a salt thereof and 40% to 5% by weight of linoleic acid or a salt thereof.

13. The method of claim 10 wherein the insect is selected from the group consisting of cabbage aphid, tent caterpillar, white fly, and earwig.

* * * * *